United States Patent [19]
Dosmann et al.

[11] Patent Number: 5,611,999
[45] Date of Patent: Mar. 18, 1997

[54] DIFFUSED LIGHT REFLECTANCE READHEAD

[75] Inventors: Andrew Dosmann, Granger; Rick J. Johnson, Elkhart, both of Ind.

[73] Assignee: Bayer Corporation, Elkhart, Ind.

[21] Appl. No.: 523,272

[22] Filed: Sep. 5, 1995

[51] Int. Cl.$^6$ ................................................. G01N 21/47
[52] U.S. Cl. ................................. 422/82.05; 422/82.09; 356/446
[58] Field of Search .................... 422/82.05, 82.09, 422/56, 57; 356/446, 244

[56] References Cited

U.S. PATENT DOCUMENTS

| | | | |
|---|---|---|---|
| 4,950,905 | 8/1990 | Butler et al. | 356/446 X |
| 5,039,225 | 8/1991 | Uekusa | 356/446 X |
| 5,139,339 | 8/1992 | Courtney et al. | 356/446 |
| 5,350,697 | 9/1994 | Swope et al. | 422/82.09 |

*Primary Examiner*—Jeffrey Snay
*Attorney, Agent, or Firm*—Roger N. Coe

[57] ABSTRACT

A diffused light reflectance readhead is disclosed. The readhead employs an improved light emitting diode (LED) providing a more strongly collimated beam of fight around a beam axis onto a reagent test pad. The reagent test pad is supported on a strip guide at an angle $\alpha$ of 5 degrees with respect to the perpendicular of the beam axis. It has been discovered that when $\alpha$ is between 3 and 8 degrees that specular reflection is dramatically reduced in relation to the small reduction in reflected light received by a sensor. The diffuse reflected light travels to the sensor by passing through a staircase optical baffle at an angle of 45 degrees to the perpendicular of the beam axis. The sensor converts the optical signal into an electrical one for processing and analysis. One embodiment of the present invention can detect the presence of glucose in a blood sample.

4 Claims, 2 Drawing Sheets

DIFFUSED LIGHT REFLECTANCE READHEAD

FIELD OF THE INVENTION

The present invention generally relates to the field of medical diagnostic equipment used in clinical chemistry. More particularly, the present invention relates to a improved diffused light reflectance readhead used as part of a visual imaging system for detecting analytes present in other substances, such as glucose in blood, on a reagent test strip.

BACKGROUND OF THE INVENTION

Reagent test strips are widely used in clinical chemistry. A reagent test strip usually has one or more test areas (pads), and each pad is capable of undergoing a color change in response to contact with an analyte in a liquid specimen. The liquid specimen is reacted with a pad on the reagent strip in order to ascertain the presence of one or more analytes, i.e., constituents or properties of interest, in the liquid specimen. The presence and concentrations of these analytes in the specimen are indicated by a color change in the pads of the test strip when reacted with the analyte. Diffuse light reflected off of the reacted reagent test strip is analyzed to determine the amount of color change. Usually, this analysis involves a color comparison between the reacted test pad and a color standard or scale. In this way, reagent test strips assist medical personnel in dignosing the existence of diseases and other health problems.

An example of a reagent test strip suitable for use with the present invention is the Glucometer Encore®—Blood Glucose Test Strips sold by Bayer Corporation, Diagnostics Division, of Elkart, Ind. 46515.

Reflected light comparisons made with the naked eye can lead to imprecise measurement. Today, reagent strip reading instruments exist that employ reflectance photometry for reading test strip changes. Some reagent strip reading instruments have readheads that contain light emitting diodes (LEDs) for illuminating reagent pads. Some of the light from the LED is reflected off of each pad while some is absorbed in such a way to indicate the color change of the pad due to its reaction with the substance of interest, such as glucose. The diffuse reflected light, i.e., the color-changed light, is detected by a sensor which converts the light into electronic signals for processing.

It has been found that present light emitting diodes (LEDs) are not ideal for use in readheads because the beam of light they produce is not very well collimated. A significant percentage of the diffused light produced by present LEDs tends to become stray light that must be filtered out.

Some prior art inventions have tried to address the problem of stray light being emitted from the LED. One approach has been to encapsulate the sides of the LED with a light absorbing material. An example of a device with such encapsulation is U.S. Pat. No. 5,122,943 by Pugh. This approach results in an LED that absorbs a portion of the light it generates in the encapsulation material.

It would be desirable to have an LED adapted for use in a readhead such that less stray light is produced that requires filtering. Moreover, it would be even more desirable to collimate more of the light that would otherwise become stray light in order to increase the signal and efficiency of the readhead.

However, even when light is fairly well collimated the problem of specular reflection effectively raises the level of "noise" in the light signal received by the sensor. Specular reflection of light is analogous to light bouncing off of a mirror wherein the overall color of the reflected light is not significantly changed. Thus, specular reflection works against sensing a color change of a pad on the reagent strip. It would be desirable to decrease the specular reflection of light received by the light sensor in order to provide a better signal-to-noise ratio.

Because stray light makes sensing the color change of a pad more difficult and less accurate, various optical baffles have been employed to filter some of the stray light. For example, a spiral threaded aperture has been used to reduce stray light. Only light coming from a narrow field of view can travel through the threaded aperture to the sensor, thus stray light is reduced. However, threaded apertures can be costly to form because they require extra manufacturing steps. One way the threaded aperture is formed is by embedding a screw-like element into the plastic as it is being molded. When the plastic has cooled the screw-like element is unscrewed in order to leave a corresponding threaded aperture. Mother threaded aperture drawback is that threaded apertures tend to have smaller diameters which reduce the total amount of light received by the sensor, which in turn impacts the sensor's accuracy. Thus, it would be desirable to have an optical baffle that reduces stray light, but is less expensive and easier to fabricate. Furthermore, it is desirable to have an optical baffle that increases the amount of desirable light received by the sensor.

SUMMARY OF THE INVENTION

The present invention is an apparatus and method for providing improved detection of analytes reacted with reagent test pads. One embodiment of the present invention provides an improved diffused light reflectance readhead used in a neonatal station as part of a visual imaging system used to detect glucose in blood samples. The visual imaging system analyzes a color change associated with one or more test pad areas on a reagent test strip following contact thereof with liquid specimen, for example, blood or urine, in order to detect analytes such as glucose, protein, blood, ketones, bilirubin, urobilinogen, nitrite, cholesterol, etc. Light reflected off of the reagent strip is converted into electrical signals that earl be analyzed with diagnostic equipment. More specifically, one embodiment of the present invention employs a new light emitting diode (LED) optimized for use with a readhead. The LED's geometry has been redesigned to increase the production of collimated light. The length between a light emitting semiconductor and a curved outer surface of the LED has been increased to more nearly bring the light emitting semiconductor to a focal point of the curved outer LED surface. Repositioning the light emitting semiconductor in this way has the effect of much more strongly collimating the emitted light, thereby reducing unwanted sway light while increasing the desirable illumination of a given reagent test pad. The present design of the LED has the effect of improving the signal-to-noise ratio of the light received by the sensor.

The reagent test strip itself is placed against a supporting surface. The surface has been tilted 5 degrees away from a plane perpendicular to the axis of the collimated beam and away from the sensor. The small 5 degree fit has the unexpectedly large effect of reducing specular reflection to the sensor by approximately a factor of 3, dramatically increasing the signal-to-noise ratio to the To further enhance the sensor's reception of diffuse reflected (color changed) light a series of steps in an aperture creating a staircase optical baffle is employed on only one side of an aperture permitting reflected light to encounter the sensor. It has been discovered that most of the undesirable light entered the baffle aperture from the side nearest the LED, where steps are now positioned, thus eliminating most of the undesirable light. The staircase baffle reduces stray light while allowing the rest of the aperture to be larger, thus allowing more diffuse reflected light to reach the sensor. The other sides of the staircase optical baffle are accordingly less modified so the baffle is easier to manufacturer in this way as well. Therefore, the staircase baffle is both easier and less costly to manufacture.

Reflected light received by a sensor is convened into electrical signals for processing. Analysis of the electronic signals is performed to determine the presence of glucose in blood. The present invention provides improved cost, manufacturing and performance advantages over current systems.

BRIEF DESCRIPTION OF THE DRAWING

Other aspects and advantages of the invention will become apparent upon reading the following detailed description and upon reference to the accompanying drawings, in which.

DETAILED DESCRIPTION OF THE PREFERRED EMBODIMENTS

Figure 1:
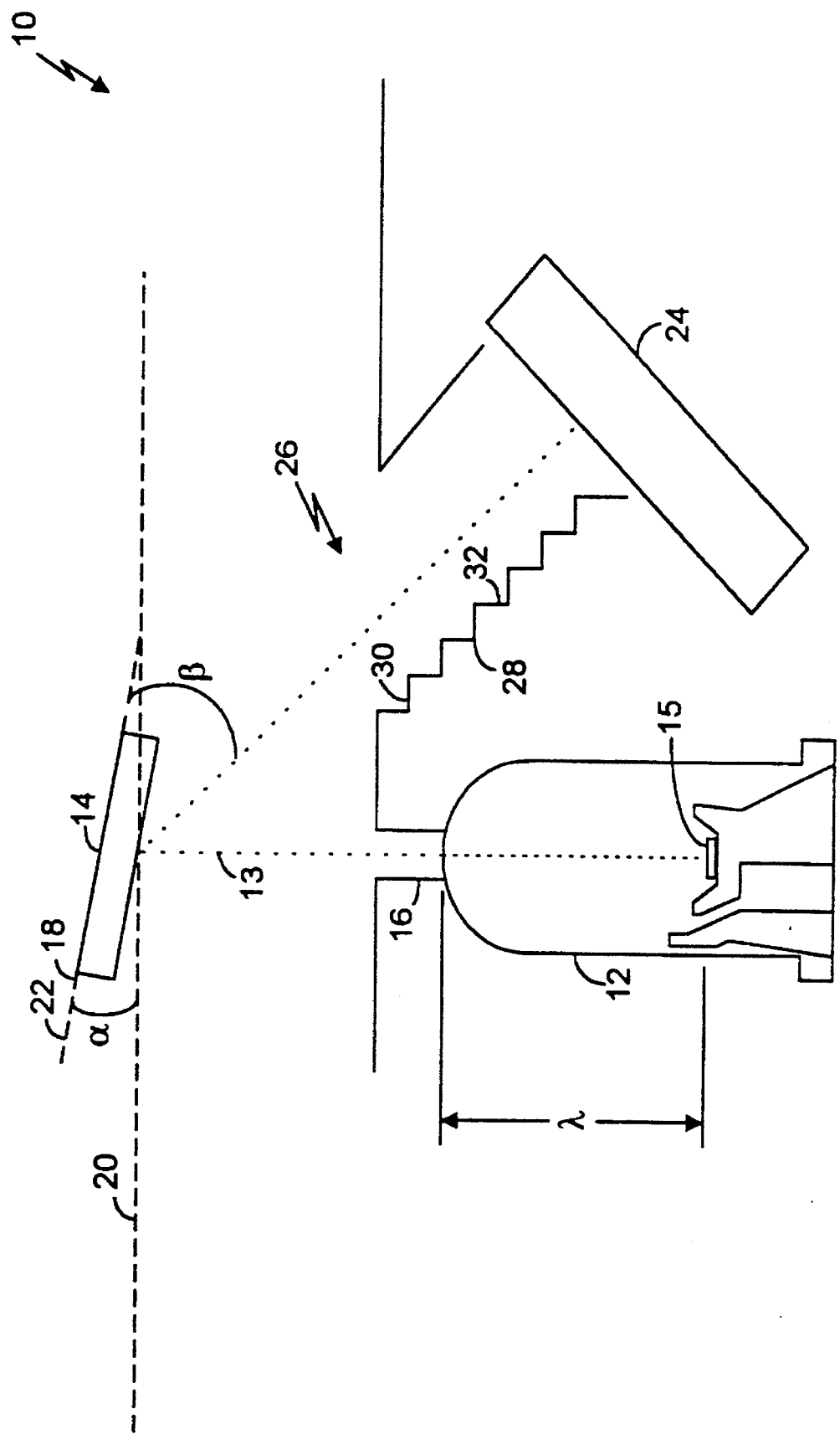
FIG. 1 is a block diagram overview of a diffused light reflectance readhead according to one embodiment of the present invention.
Figure 3:
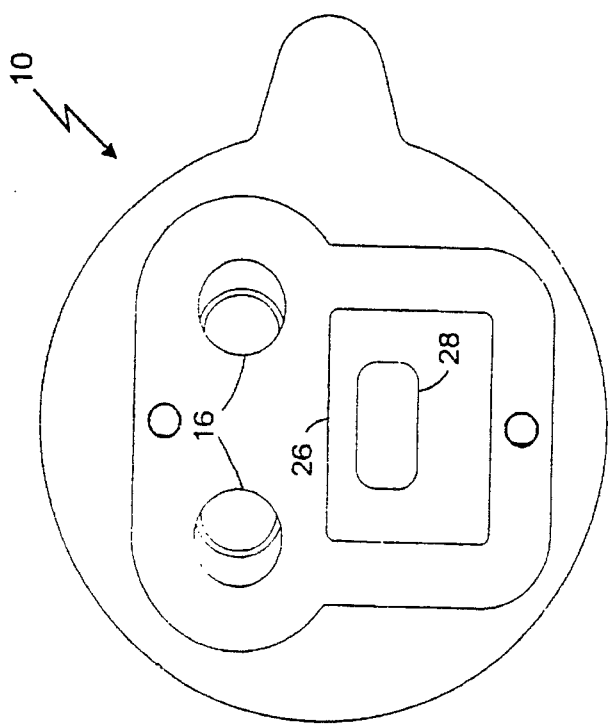
FIG. 3 is a bottom plan view of a diffused light reflectance readhead according to one embodiment of the present invention.

While the invention is susceptible to various modifications and alternative forms, a number of specific embodiments thereof have been shown by way of example in the drawings and will be described in detail herein. It should be understood, however, that this is not intended to limit the invention to the particular forms disclosed. On the contrary, the intention is to cover all modifications, equivalents and alternatives falling within the spirit and scope of the invention as defined by the appended claims.

One embodiment of the present invention is used in an neonatal medical diagnostic instrument to measure diffused light reflected from reagent paper that has been reacted with specimen containing an analyte, such as blood containing glucose.

In FIGS. 1–4, a diffused light reflectance readhead 10 is designed with one or more improved light emitting diodes (LEDs) 12 to reflect light 13 off of a reagent test pad reacted with an analyte 14. The LEDs 12 are pulsed on and off using a constant-current pulsed direct current (DC) power supply (not shown). Pulsing the LEDs 12 minimizes heating as well as associated light 13 intensity and wavelength variation.

It has been discovered that collimated light is desirable for analysis purposes, while uncollimated light is not desirable because it tends to produce stray light. Furthermore, it was also discovered that the LED's 12 curved outer surface in its epoxy casing acts as a lens to some degree. The present invention takes advantage of the lensing effect by relocating a light emitting semiconductor die 15 (also commonly known as a "chip") inside the LED 12 to a position approximately at the focal point of the curved outer surface. Computer modeling and experimental results were used to obtain an optimum tip-to-die distance ($\lambda$) of 0.170±0.01 inch for this configuration. Note that other distances for $\lambda$ can be used but are not considered optimal.

The present invention reduces the light's 13 resultant illumination spot size on the reagent strip 14. A significant portion of the spot size is less than 0.100 inch in diameter at a distance of 0.150 inch beyond the readhead surface. Because the spot size is reduced the need for a focusing lens is eliminated, thus saving its cost.

Another advantage of the present LED 12 design is that it decreases the readhead's sensitivity to mechanical vibrations and die 15 centering errors. A standard T1 LED, for example, has a die-to-tip distance ($\lambda$) of about 0.100 inch. As $\lambda$ is increased to approach the focal point of the standard T1 LED the light 13 out from the standard LED becomes more collimated. This tends to produce a smaller spot for an equivalent aperture size. The smaller spot size and increased collimation has the advantage of making the readhead less sensitive to positioning of the die 15 within the LEDs 12. Thus, if the LEDs' 12 die 15 is not placed at the center of the LEDs 12, the output spot position will be shifted a smaller mount in proportion to the die 15 centering error.

Other factors were considered in the design of the LEDs 12. Each LED 12 and each illumination aperture 16 associated with that LED 12 must illuminate a spot of the proper size and intensity. The significant portion of the spot size should be less than the pad size to reduce generation of stray light. Generally, greater intensity is desirable because signal strength is increased. Furthermore, the LEDs 12 have their sides coated with a light absorbing material to further reduce stray light as is known in the arts. The total effect is approximately a 200–300 percent signal improvement over prior LEDs used in readheads.

Light 13 from the LEDs 12 travel through the illumination apertures 16 to the reagent pad 14 on a reagent test strip guide 18, It is known to have the strip guide 18 hold the reagent strip 14 perpendicular to the axis of the collimated light 13 emitted from the LED 12. Note that in FIG. 1 $\alpha$ defines the angle between a perpendicular plane 20 that is perpendicular to the axis of the collimated beam and a guide plane 22 that is parallel to the orientation of the strip guide 18, which is zero degrees in the prior art. It has been found that tilting the strip guide 18 with the associated reagent pad 14 in a direction away from a light sensor 24 by only 5 degrees, i.e., $\alpha$ is equal to 5 degrees, produced the unexpected benefit of reducing specular reflection received by the sensor 24 by approximately a factor of three. It was unexpected that such a small change in angle $\alpha$ would produce such a large decrease in specular reflection. Furthermore, the large reduction of specular reflection enabled the LEDs 12 and the light sensor 24 to be located in closer proximity to one another than currently possible, thereby reducing the size of the reflectance photometer. In one embodiment the sample to detector distance is approximately 0.4 inch, which is one half of some current readheads, thus providing an increase in signal by about a factor of 4. Moreover, the reduction in spectral reflection enabled the viewing area of the light sensor 24 to engendering significant improvements in the readhead's 10 sensitivity to variations in reagent strip 14 height variations.

The optimal range of angle a has been found to approximately range between 3 degrees and 8 degrees for reagent test strips 14 reacted with blood containing glucose, however, the range should be similar for other analytes as well. When angle α becomes less than 3 degrees the reduction in specular reflection becomes relatively small. Conversely, when angle α becomes greater than 8 degrees then desirable diffuse color reflection is reduced, along with undesirable specular reflection, to the point that significant signal loss begins to occur. Note that if α is less than 3 degrees or greater than 8 degrees the readhead 10 will still perform, however, not optimally.

Figure 4:
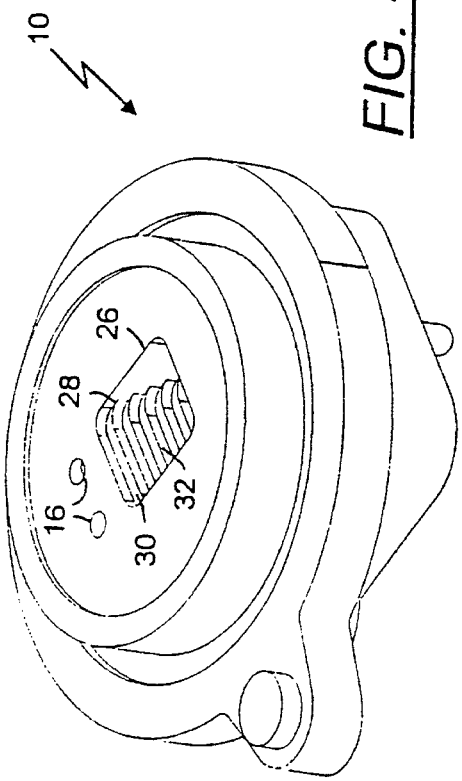
FIG. 4 is a isometric plan view of a diffused light reflectance readhead according to one embodiment of the present invention.
Figure 2:
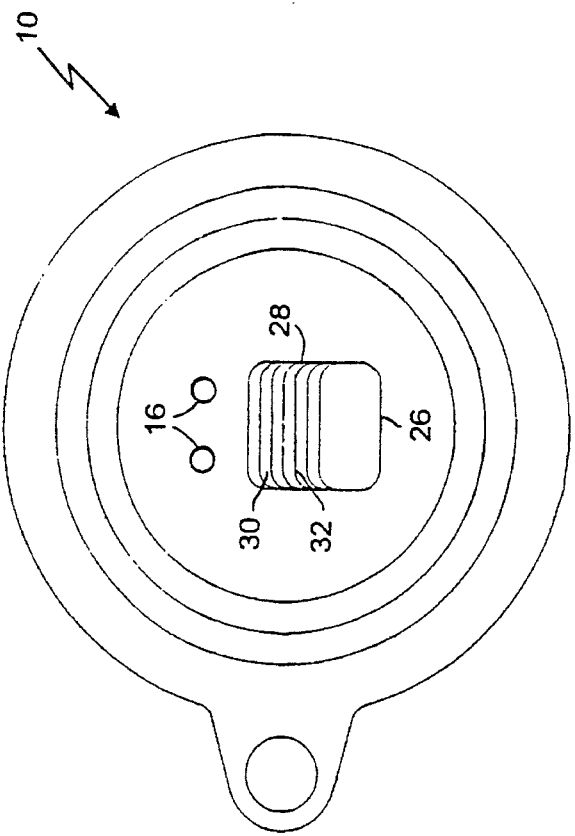
FIG. 2 is a top view of a diffused light reflectance readhead according to one embodiment of the present invention.

In FIG. 1, after light 13 from the LEDs 12 is reflected off of the reagent pad 14 it passes through a staircase baffle 26 at an angle β of approximately 45 degrees to the perpendicular plane 20 before reaching the sensor 24. As shown in FIGS. 1, 2 and 4, the staircase baffle 26 has a series of steps 28 primarily on one side. In one embodiment each step's top side 30 and vertical side 32 (both steps 28 and sides 30,32 are representatively marked), are approximately of equal length and positioned at a 90 degree angle to each other. It has been found that the length of each step side 30,32 works best to eliminate stray light and pass desirable diffuse reflected light 13 when sized between 0.010 inch and 0.030 inch. Furthermore, step 28 size is practically limited to something smaller than would extend into the 12 or the illumination apertures 16. In one embodiment the length of each step side 30,32 was chosen to be 0.020 inch. The number of steps 28 is not fixed but desirably there are a sufficient number of steps 28 to extend the entire length of the staircase baffle 26. The total length of the staircase baffle 26 is a function of geometry. Manufacturing limitations set a minimum separation distance between the LEDs 12 and the light sensor 24. Knowing the minimum separation distance and the distance from the LEDs 12 to the reagent test pad 14 along with the fact that the steps 28 are at an angle β of 45 degrees allows a simple calculation of the distance the steps 28 must cover. Thus, in one embodiment there are 7 individual steps. 28 as illustrated in FIGS. 1, 2 and 4.

The steps 28 are positioned on a side of staircase baffle 26 closest to the LEDs 12. This is because it has been found that most of the stray light enters an aperture leading to the sensor 24 on the close side and that having the steps there filters out most of stray light.

A key advantage to the use of steps 28 for the staircase baffle 26 is the ease in manufacture over the prior art. Steps 28 can easy be formed from a mold while prior art threads are not so easily formed in the readhead 10 material.

Once reflected light 13 passes through the staircase baffle 26 it reaches the light sensor 24. Note that no transfer optics are required between the reagent pad 14 and the sensor 24 because of the design advantages of the present invention.

Devices that can be employed as the sensor 24 include charge coupled devices (CCDs), photocells and photodiodes. In one embodiment of the present invention a OPT101W-R sensor from Burr-Brown, International Airport Industrial Park, 6730 South Tucson Blvd., Tucson, Ariz. 85706, is employed as the light sensor 24. The sensor 24 has an electrical response that is proportional to the reflected light 13 received. The electrical response is interpreted by processing electronics (not shown). The processing electronics convert the analog electrical response of the sensor 24 into digital dam. The processing electronics also include a microprocessor (not shown) which stores and utilizes the digital data to calculate contrast variations indicated by the sensor 24. In one embodiment, the change in color is used to determine a concentration of glucose in a blood sample.

Thus, there has been described herein a diffused light reflectance readhead 10.

Many modifications and variations of the invention as hereinbefore set forth can be made without departing from the spirit and scope thereof and therefore only such limitations should be imposed as are indicated by the appended claims.

What is claimed is:

1. A diffused light reflectance readhead for detecting diffuse light reflected off of a reagent test pad reacted with an analyte, comprising:

illuminating means having a beam axis for illuminating said reagent test pad;

supporting means for supporting said reagent test pad at an angle a within an approximate range of 3 to 8 degrees with respect to a perpendicular of said illuminating means beam axis;

optical detector means for receiving and detecting said light reflected off of said reagent test pad, said optical detector means converting said light into corresponding electrical signals, said optical detector means positioned such that an axis through which light is received by said optical detector means is at a greater acute angle to an axis perpendicular to said reagent test pad than said illuminating means beam axis; and interpretation means for interpreting said corresponding electrical signals to detect the presence of a substance of interest in an analyte.

2. The diffused light reflectance readhead of claim 1 wherein said supporting means supports said reagent test pad at an angle α of approximately 5 degrees.

3. The diffused light reflectance readhead of claim 1 wherein said optical detector means further comprises a light sensor positioned at an angle β of approximately 45 degrees with respect to said perpendicular of said illuminating means beam axis.

4. The diffused light reflectance readhead of claim 1 wherein said readhead detects the presence of an analyte when a reagent test pad is reacted with a sample of body fluid.

* * * * *